(12) United States Patent
Isgut

(10) Patent No.: US 10,041,109 B2
(45) Date of Patent: Aug. 7, 2018

(54) METHOD FOR DETECTION OF A NUCLEIC ACID TARGET SEQUENCE

(71) Applicant: TotemID Inc., Atlanta, GA (US)

(72) Inventor: Monica Isgut, Atlanta, GA (US)

(*) Notice: Subject to any disclaimer, the term of this patent is extended or adjusted under 35 U.S.C. 154(b) by 0 days.

(21) Appl. No.: 15/130,301

(22) Filed: Apr. 15, 2016

(65) Prior Publication Data

US 2016/0304943 A1 Oct. 20, 2016

Related U.S. Application Data

(60) Provisional application No. 62/148,975, filed on Apr. 17, 2015.

(51) Int. Cl.
*C12Q 1/68* (2018.01)
*C12Q 1/6837* (2018.01)
*C12Q 1/6816* (2018.01)
*C12Q 1/6897* (2018.01)

(52) U.S. Cl.
CPC ......... *C12Q 1/6837* (2013.01); *C12Q 1/6816* (2013.01); *C12Q 1/6897* (2013.01)

(58) Field of Classification Search
CPC .... C12Q 1/6837; C12Q 1/6816; C07H 21/04; C12N 15/113; C12N 15/67
See application file for complete search history.

(56) References Cited

FOREIGN PATENT DOCUMENTS

WO   WO 2014/074648   *   5/2014
WO   WO 2015/085209   *   6/2015

OTHER PUBLICATIONS

Altan-Bonnet et al, Robust sequence discrimination, 2012, Nature Chemistry, 4, 155-157.*

* cited by examiner

*Primary Examiner* — Narayan Bhat
(74) *Attorney, Agent, or Firm* — Yuri L. Eliezer; Bekiares Eliezer LLP

(57) ABSTRACT

Disclosed is a method of facilitating detection of a nucleic acid target sequence. The method may include utilizing a toehold-mediated DNA strand displacement apparatus comprising a portion complementary to the nucleic acid target sequence. The method may further include utilizing a RNA toehold switch comprising a RNA sequence. Further, the toehold portion of the RNA sequence may be complementary to a portion of the toehold-mediated DNA strand displacement apparatus. The method may further include combining the toehold-mediated DNA strand displacement apparatus and the RNA toehold switch in an assay, such that the two are never in direct physical contact with each other. Accordingly, a sample containing the nucleic acid target sequence on the substrate may displace a nucleic acid strand from the toehold-mediated DNA strand displacement apparatus and bind a portion of it to the RNA toehold switch resulting in expression of the reporter protein.

19 Claims, 7 Drawing Sheets

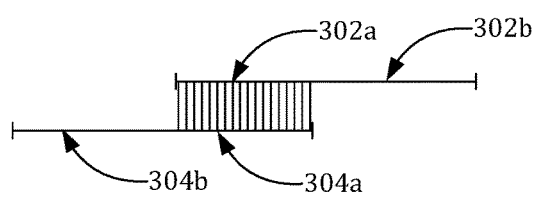 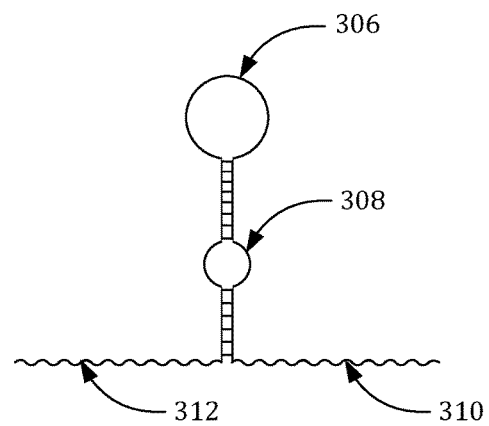
*FIG. 3A*  *FIG. 3B*

METHOD FOR DETECTION OF A NUCLEIC ACID TARGET SEQUENCE

RELATED APPLICATION

Under provisions of 35 U.S.C. § 119(e), the Applicant claims the benefit of U.S. provisional application No. 62/148,975, filed Apr. 17, 2015, which is incorporated herein by reference.

It is intended that each of the referenced applications may be applicable to the concepts and embodiments disclosed herein, even if such concepts and embodiments are disclosed in the referenced applications with different limitations and configurations and described using different examples and terminology.

It should be noted that a plurality of appendices are attached to the provisional application from which this present application claims priority. The appendices disclose a plurality of embodiments, as well apparatus and methods associated therewith. Such embodiments are herein incorporated into the present disclosure as part of the detailed description below. Applicant reserves all rights to expressly incorporate the disclosure of the appendices in the present application or any future patent application filed claiming priority to the present application.

FIELD OF DISCLOSURE

The present disclosure generally relates to detection of a nucleic acid target sequence. More specifically, the present disclosure relates to a method, apparatus and array for facilitating detection of a nucleic acid target sequence using a toehold-mediated DNA strand displacement apparatus and a RNA toehold switch.

BACKGROUND

In some situations, nucleic acid target sequence detection is needed for medical and research applications. For example, it may be used in personalized medicine to prescribe the most effective drug for a patient based on his or her genetic make-up. Nucleic acid target sequence detection may also be helpful in diagnosing certain infectious diseases by distinguishing between different strains of pathogens. It may also be used in a variety of research studies that involve understanding specific allele sequences present in an individual or model organism. The conventional strategy to detect nucleic acid target sequences is to use methods that require expensive machinery or the use of expensive materials such as fluorescent probes. For example, DNA target sequence detection using a conventional Taqman assay may sometimes be multiple times more expensive than the method described herein.

Accordingly, there is a need for lower cost methods for facilitating detection of target sequences corresponding to nucleic acid strands such as, for example, RNA and single stranded DNA (ssDNA).

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

Embodiments of the present disclosure may provide an inexpensive and accurate SNP typing method, apparatus, and system that can be applied for point-of-care use outside the lab. Embodiments may enable a coupling of two already existing techniques, the toehold-mediated DNA strand displacement reaction and the RNA toehold switch, and embedding it on porous materials such as paper that allow portability.

Further, embodiments of the present disclosure also provide a method of facilitating detection of a nucleic acid target sequence. For instance, the nucleic acid target sequence may correspond to a RNA and/or a single stranded DNA. Further, the nucleic acid target sequence may include a single nucleotide polymorphisms (SNP) genotype.

The method may include obtaining a Toehold-mediated DNA strand displacement apparatus comprising a retainer strand and a release strand. The first portion of the retainer strand may be complementary to a first portion of the release strand. Accordingly, the retainer strand and the release strand may be bound together at the first portion. Further, a second portion of the retainer strand may be complementary to the nucleic acid target sequence. Further, the second portion of the retainer strand may be distinct from the first portion of the retainer strand. Likewise, the second portion (trigger portion) of the release strand may be distinct from the first portion of the release strand. Accordingly, subsequent to binding of the retainer strand and the release strand, the second portion of each of the retainer strand and the release strand may be overhanging.

The method may further include obtaining a RNA toehold switch including an RNA sequence. Further, the RNA sequence may include an inverted loop with a sequestered ribosome binding site, a translation start codon and a transducer sequence coding for a reporter protein. Throughout the various embodiments of the present disclosure, the referenced term "inverted loop" may also correspond to, as known to one of ordinary skill in the field of the present disclosure, a "stem domain," and, in various embodiments, may be fully or partially double-stranded. For example, in some embodiments, an invert loop may be comprised of loop portions (which may be protruding) and stem portions (which may be bound together via hybridization). Accordingly, in some embodiments, as would be understood by one of ordinary skill in the field of the present disclosure, the ribosome binding site and translation start codon may be sequestered either within one or more loop portions of the "inverted loop" or within one or more the stem portions of the "inverted loop." The reporter protein may include, but is not limited to, one or more of Beta-galactosidase and Green Fluorescent Protein (GFP). Further, a toehold portion of the RNA sequence may be complementary to the second portion of the second nuclei acid strand of the Toehold-mediated DNA strand displacement apparatus. Accordingly, the release strand may be configured to bind with the RNA toehold switch at the toehold portion.

Additionally, the method may include combining each of toehold-mediated DNA strand displacement apparatus and the RNA toehold switch in an assay such that they are never in direct contact with each other but such that when a nucleic acid target sequence complementary to both the first portion and the toehold portion of the retainer strand is present, the release strand is displaced and may travel to the RNA toehold switch, after which the trigger portion of the release strand binds to the toehold portion of the RNA toehold switch, which leads to the collapse of the RNA toehold switch, allowing for the expression of a reporter protein.

For instance, in some embodiments, the combining may include embedding each of the toehold-mediated DNA strand displacement apparatus and the RNA toehold switch on a substrate 104, as exemplarily illustrated in FIG. 1A-1B. For instance, the substrate 104 may include a paper based material that may be freeze dried. Further, the substrate 104 may include a cell extract configured to facilitate expression of the reporter protein. For example, the cell extract may include S30 cell extract.

In another instance, the combining may include allowing fluid to flow between the toehold mediated DNA strand displacement apparatus and the RNA toehold switch. For example, such a phenomenon may be allowed to take place in a microfluidic device. Accordingly, the toehold-mediated DNA strand displacement apparatus may be contained in a first chamber of the microfluidic device. Further, the RNA toehold switch may be contained in a second chamber of the microfluidic device. Moreover, the first chamber may be spatially separated from the second chamber. Furthermore, a flow of contents from the first chamber to the second chamber may be unidirectional. Accordingly, diffusion of the contents of the fluid from the second chamber back into the first chamber may be eliminated and/or minimized.

Further, in some embodiments, the method may further include assembling a plurality of substrates in an array. The plurality of substrates may be partitioned using a demarcation material, such as for example, but not limited to, a wax based ink. Additionally, a first substrate of the plurality of substrates may be configured to detect a first nucleic acid target sequence. Further, a second substrate of the plurality of substrates may be configured to detect a second nucleic acid target sequence. Accordingly, in some instances, the array may be capable of simultaneously detect multiple distinct nucleic acid target sequences.

In some embodiments, the method may further include generating the toehold-mediated DNA strand displacement apparatus based on a hybridization process of a DNA oligo with a RNA oligo. Accordingly, a portion of the DNA oligo may be complementary to the nucleic acid target sequence. Further, a portion of the RNA oligo may be complementary to the toehold portion of the RNA sequence comprised in the RNA toehold switch.

Further, in some embodiments, the method may additionally include obtaining a specimen comprising the sample. Furthermore, the method may include subjecting the specimen to each of DNA extraction, DNA denaturation, and DNA fragmentation. Accordingly, single nucleic acid strands containing the nucleic acid target sequence may be generated. Alternatively, in case the specimen includes RNA, the specimen may be subjected to RNA extraction and RNA strand separation. Furthermore, the method may be conducted at ambient temperatures without the need for external machinery.

Additionally, the method may further include introducing a sample comprising the nucleic acid target sequence onto the substrate. Accordingly, binding of the nucleic acid target sequence to second portion of the retainer strand may displace the release strand. Further, the second nucleic strand may bind to the RNA toehold switch resulting in unwinding of the inverted loop, exposure of the sequestered ribosome binding site and translation of the reporter protein.

Accordingly, in some embodiments, the method may further include detecting presence of the reporter protein using an electronic reader. The presence of the reporter protein may be indicative of detection of the nucleic acid target sequence. Furthermore, the method may include communicating detection of the reporter protein to a computing device, such as for example a smartphone and/or a desktop computer. Accordingly, further analysis of detection of the nucleic acid target sequence may be performed. Alternatively, presence of the reporter protein may also be detected based on visual inspection by eye. For instance, the reporter protein may react with one or more chemicals present in the substrate leading to a colorimetric change in the substrate which may be visible in plain sight.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the Applicants. The Applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings:

FIG. 3A illustrates a structure of a Toehold-mediated DNA strand displacement apparatus for facilitating detection of a nucleic acid target sequence in accordance with some embodiments;

FIG. 3B illustrates a structure of a RNA toehold switch for facilitating detection of a nucleic acid target sequence in accordance with some embodiments;

DETAILED DESCRIPTION

Figure 1A:
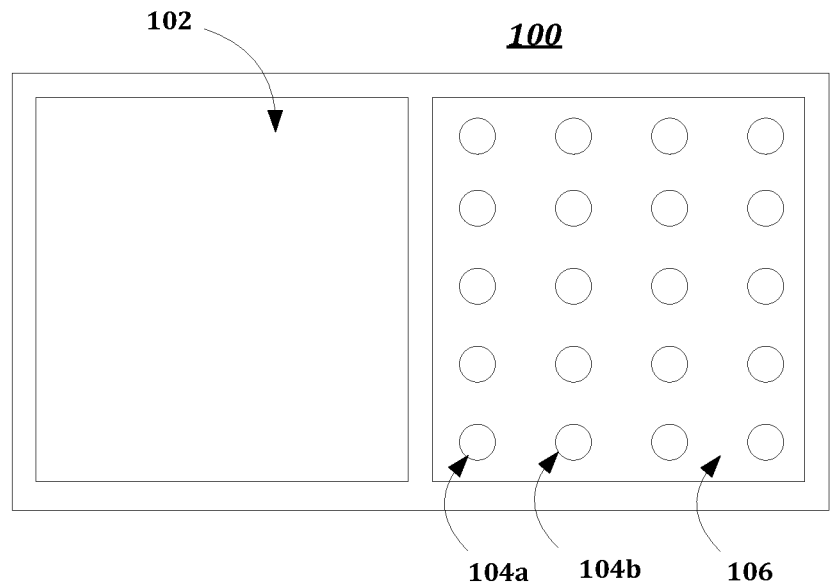
FIG. 1A illustrates a top view of an array for facilitating detection of a nucleic acid target sequence in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of SNP genotyping, embodiments of the present disclosure are not limited to use only in this context.

I. Overview

Consistent with embodiments of the present disclosure, an apparatus 100 may be provided. This overview is provided to introduce a selection of concepts in a simplified form that are further described below. This overview is not intended to identify key features or essential features of the claimed subject matter. Nor is this overview intended to be used to limit the claimed subject matter's scope.

The apparatus 100 may be used by individuals or companies to detect one or more nucleic acid target sequences corresponding to nucleic acid strands, such as, for example, DNA and/or RNA in a specimen, such as, for example, blood, saliva, bodily tissues, bone marrow, etc. Although the presented embodiments reference nucleic acid strands, it should be understood that nucleic acid strand is used as an example and that the embodiments may be applicable to other similar compounds.

FIG. 1A illustrates a top view of the apparatus 100 configured to detect a nucleic acid target sequence. In some embodiments, the nucleic acid target sequence may include a SNP genotype. Accordingly, the apparatus 100 may be configured to receive a sample including the nucleic acid target sequence.

Further, in some embodiments, the apparatus 100 may include a cell lysis and DNA denaturation unit 102 which may be configured to receive a specimen, such as, for example, blood, saliva, bodily tissues, bone marrow, etc. including the sample. Furthermore, the cell lysis and DNA denaturation unit 102 may be configured to subject the specimen to each of DNA extraction, DNA denaturation, and DNA fragmentation. Accordingly, single nucleic acid strands containing the nucleic acid target sequence may be generated by the apparatus 100. Alternatively, in case the specimen includes RNA, the specimen may be subjected to RNA extraction and RNA strand separation.

Further, the apparatus 100 may include a substrate 104 configured to detect presence of the nucleic acid target sequence. For instance, the substrate 104 may include a paper based material that may be freeze dried. Further, the substrate 104 may include a cell extract configured to facilitate expression of a reporter protein. For example, the cell extract may include S30 cell extract.

Additionally, in some embodiments, the apparatus 100 may include an array 106 comprising a plurality of substrates 104. For instance, in some embodiments, the plurality of substrates 104 may be assembled in the form of the array 106. The plurality of substrates 104 may be partitioned using a demarcation material, such as for example, but not limited to, a wax based ink. Additionally, a first substrate 104a of the plurality of substrates 104 may be configured to detect a first nucleic acid target sequence. Further, a second substrate 104b of the plurality of substrates 104 may be configured to detect a second nucleic acid target sequence. Accordingly, in some instances, the array 106 may be configured to simultaneously detect multiple, distinct nucleic acid target sequences.

Further, the substrate 104 may be embedded with each of a toehold-mediated DNA strand displacement apparatus, a RNA toehold switch and a cell extract configured to facilitate expression of a reporter protein.

In some embodiments, the toehold-mediated DNA strand displacement apparatus, as exemplarily illustrated in FIG. 3A, may include a retainer strand 302 and a release strand 304. A first portion 302a of the retainer strand 302 may be complementary to a first portion 304a of the release strand 304. Accordingly, the retainer strand 302 and the release strand 304 may be bound together at the first portions 302a and 304a. Further, a second portion 302b of the retainer strand (toehold portion) 302 may be complementary to the nucleic acid target sequence (not shown in figure). Further, the toehold portion 302b of the retainer strand 302 may be distinct from the first portion 302a of the retainer strand 302. Likewise, the second portion (trigger portion) 304b of the release strand 304 may be distinct from the first portion 304a of the release strand 304. Accordingly, subsequent to binding of the retainer strand 302 and the release strand 304, the second portions 302b and 304b may be overhanging as illustrated.

Further, in some embodiments, the RNA toehold switch, as illustrated in FIG. 3B, may include an RNA sequence. It is to be understood from the present disclosure that such reference to FIG. 3B is a reference to one possible embodiment, and that sequestration is not required to be through inner loops of the inverted loop, but can also be enabled via, for example, hybridization. Further, the RNA sequence may include an inverted loop with a sequestered ribosome binding site 306, a sequestered translation start codon 308, a transducer sequence coding 310 for a reporter protein located on the 3' side of the inverted loop, and a toehold portion located on the 5' end of the inverted loop. In some embodiments, the reporter protein may include, but is not limited to, one or more of beta-galactosidase and Green Fluorescent Protein (GFP). Further, if beta-galactosidase is used for a colorimetric assay, one or more chemicals may be added to the substrate so that beta-galactosidase can react with the one or more chemicals to produce a color change. Further, a toehold portion 312 on the 5' side of the inverted loop of the RNA sequence may be complementary to the second portion 304b of the second nuclei acid strand 304 of the toehold-mediated DNA strand displacement apparatus. Accordingly, the trigger portion of the release strand 304 may be configured to bind with the RNA toehold switch at the toehold portion 312.

Additionally, the apparatus 100 may be configured to introduce a sample comprising the nucleic acid target sequence onto the substrate 104. For instance, as illustrated in the perspective view in FIG. 2, the apparatus 100 may include a specimen collection unit configured to receive the sample. Further, the specimen collection unit may be configured to be inserted into a hollow portion of the apparatus 100 as shown. Accordingly, upon introduction of the sample on the substrate 104, binding of the nucleic acid target sequence to the second portion 302b of the retainer strand 302 may displace the release strand 304. Further, the second nucleic strand 304 may bind to the RNA toehold switch resulting in unwinding of the inverted loop, exposure of the sequestered ribosome binding site 306 and translation of the reporter protein.

Figure 2:
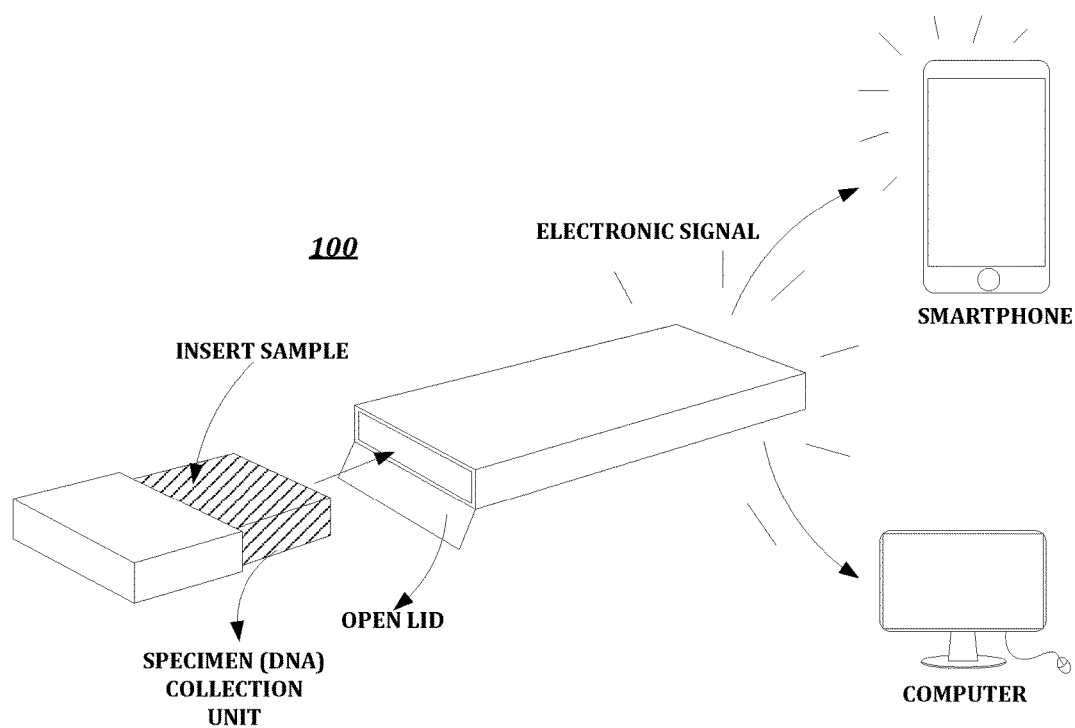
FIG. 2 illustrates a perspective view of an array for facilitating detection of a nucleic acid target sequence in accordance with some embodiments.

Accordingly, in some embodiments, the apparatus 100 may further include an electronic reader 108 configured to detect presence of the reporter protein. The presence of the reporter protein may be indicative of detection of the nucleic acid target sequence. Furthermore, the method may include communicating detection of the reporter protein to a computing device, such as for example a smartphone and/or a desktop computer as illustrated in FIG. 2. Accordingly, further analysis, such as for example, SNP genotyping based on detection of the nucleic acid target sequence may be performed.

Alternatively, presence of the reporter protein may also be detected based on visual inspection by eye. For instance, the reporter protein may react with one or more chemicals present in the substrate leading to a colorimetric change in the substrate which may be visible in plain sight.

Additionally, in some embodiments, the retainer strand may be bound to a bead, which may then be freeze dried along with the cell extract and embedded in paper. In some embodiments, the retainer strand may have a Poly A linker which can hybridize to beads with Poly T linkers. Furthermore, in some embodiments, the bead may consist of polystyrene.

EXAMPLE EMBODIMENTS

Nucleic acid target sequence detection is usually expensive and time-consuming, and is therefore not conducible for rapid point-of-care applications. Embodiments of the present disclosure allow for relatively cheap and accurate detection of nucleic acid target sequences, by using materials that can be embedded in paper and other porous substances for easy use in the field rather than only the laboratory.

Embodiments of the present disclosure may provide a toehold-mediated DNA strand displacement reaction coupled with an RNA toehold switch. This coupled system may be SNP-sequence specific and embedded into a freeze-dried paper based material that can be assembled into a custom array for multiplexing.

The toehold-mediated DNA strand displacement set-up may be comprised of a single-stranded DNA probe that is hybridized to a partially complementary DNA strand, leaving a single-stranded region called the toehold. This partially complementary strand has an overhanging RNA sequence.

The RNA toehold switch may be configured separately. The RNA toehold switch may be comprised of a) an inverted loop with a sequestered ribosome binding site and a sequestered translation start codon, b) a transducer sequence coding for a reporter protein, and c) a toehold sequence complementary to the aforementioned overhanging RNA sequence of the other set-up. Both the toehold-mediated DNA strand displacement apparatus and the RNA toehold switch are located in close proximity to each other but never physically in contact.

Once a sample with target nucleic acid sequence from a sample is added to the assay, the set of reactions begins. The target nucleic acid sequence, which may be single stranded, may bind to its complementary bases on the toehold region of the retainer strand on the toehold-mediated DNA strand displacement apparatus to initiate hybridization. If the sample sequence is fully complementary to that of the probe strand, it may displace the release strand originally bound to the probe. The trigger portion of the release strand binds to its complementary sequence on the RNA toehold switch, and this sequence is the toehold portion of the RNA toehold switch. Once it binds, the loop collapse and the ribosome binding site and translation start codon may be exposed, allowing for translation to initiate. The translation is facilitated by the presence of a cell free extract and other materials. Translation of the reporter protein, for example GFP or beta-galactosidase, may continue constitutively and the signal is robust after a few hours.

In a multiplex array for genotyping, each reaction chamber is made for a specific SNP sequence and the reporter protein can be detected on the chamber, either visually or by an electronic reader, if the given SNP sequence is present in the sample.

Embodiments of the present disclosure may allow for SNP sequencing at ambient temperatures while minimizing the need for expensive fluorescence probes, expensive machinery, and reactions such as PCR. Therefore, embodiments of the present disclosure may have the potential of being cheaper than currently existing nucleic acid target sequence detection technologies. The toehold-mediated DNA strand displacement apparatus may allow for accurate hybridization, and the RNA toehold switch allows for continuous production of reporter protein for a robust signal without the need for PCR.

Embodiments of the present disclosure may be viable at room temperature and can be embedded in paper. It is also relatively easy to design because both the trigger sequence of the toehold-mediated DNA strand displacement apparatus and the entire RNA toehold switch may be arbitrary and identical in each assay set-up, regardless of the target sequence of choice. One difference between assay set-ups designed for different nucleic acid target sequences may lie in the first and toehold portions of the retainer strand of the strand displacement setup.

Toehold-mediated strand displacement and RNA toehold switch assays have been done before, but they have not been combined and used for the low cost detection of RNA and DNA sequences. Toehold-mediated strand displacement reactions are usually used in synthetic DNA circuits. Embodiments of the present disclosure may be distinguished from the aforementioned at least because they may have an overhanging DNA sequence (the trigger of the release strand) that is displaced and binds to the toehold region of the toehold switch. Thus, with this invention, the two existing apparatuses are intimately combined to form one functional low cost assay. The RNA toehold switch for reporter protein production has been used to detect RNA sequences. Embodiments of the present disclosure test for DNA sequences and use the toehold switch as a method for signal detection.

The specificity of detection using the currently existing RNA toehold switch is currently limited, especially for single nucleotide polymorphisms. This is because the loop setup is easily collapsible. That is why the embodiments of the present disclosure make use of the high specificity of the toehold-mediated strand displacement reaction.

The toehold-mediated strand displacement reaction has previously been combined with a method involving fluorescent probes to detect the signal. However, when combined with the RNA toehold switch, the signal detection can be much lower cost.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and subcombinations described in the detailed description.

II. Configuration

Embodiments of the present disclosure may be configured in a plurality of different ways. They may contain components coupled to each other in a plurality of different sequences and arrangements. The present disclosure provides one possible embodiment of such configuration. Moreover, the present disclosure discloses a plurality of actions which may be performed by systems and apparatus available to one of ordinary skill in the field of the present disclosure. It is contemplated that any suitable means may be used, such as, for example, a portable device that chemically lyses cells and denatures DNA, allows for hybridization onto the invented array, and then detects SNP patterns and relays them electronically to a computer or smart phone. The invented hybridization array is disposable and may be able to be replaced within a device.

Although embodiments have been described to operate in a particular order, it should be understood that, in some embodiments, different operations may be performed by different elements. Moreover, an apparatus may be employed in the performance of some or all of the stages. The apparatus may comprise a cell-lysing and DNA-denaturation microfluidic component, as well as a hybridization array component which contains the invented synthetic toehold switch design embedded in discs, and an electronic sensor component to detect signals from the array.

Although embodiments have been described to be performed in conjunction with the apparatus, it should be understood that other components and devices may be used to perform the various stages. Furthermore, in some embodiments, different operations may be performed by different elements in operative communication with the apparatus.

Although the stages are disclosed in a particular order, it should be understood that the order is disclosed for illustrative purposes only. Stages may be combined, separated, reordered, and various intermediary stages may exist. Accordingly, it should be understood that the various stages may be, in various embodiments, performed in arrangements that differ from the ones described. Moreover, various stages may be added or removed without altering or deterring from the fundamental scope of the depicted methods and systems disclosed herein.

For example, in some embodiments, a PCR amplification of synthetic DNA oligos complementary to the chosen SNP sequences, for the probe sequence may be provided. Then PCR amplification of synthetic DNA oligos for the DNA part of the Toehold-mediated DNA strand displacement apparatus complementary to the probe sequence may be provided. Then a RT-PCR to separately amplify the RNA sequence of the hybrid into cDNA may be provided. Denature the cDNA and transcribe the RNA sequences may use S30 cell extract. Then, the DNA to the RNA may be ligated using a ligase, to create the Toehold-mediated DNA strand displacement apparatus. The Toehold-mediated DNA strand displacement apparatus may be hybridized to the DNA probe. The Toehold-mediated DNA strand displacement apparatus may also be ordered commercially.

The synthetic RNA toehold cassette may be amplified with the toehold region being complementary to the RNA of the hybrid, and this may be ligated to RNA for the reporter gene. The RNA toehold switch and RNA sequence of the Toehold-mediated DNA strand displacement apparatus may arbitrary and can be the identical for each SNP sequence to be tested. Column purification should be performed.

Each coupled toehold-mediated DNA-RNA strand displacement and RNA toehold switch reaction, amplified, may be embedded into a paper based material with a cell extract. The paper based materials may be freeze-dried. Wax-based ink can be used as a hydrophobic barrier to separate reaction spaces into compartments, and can be printed into an array format. One paper based material may be provided in each compartment. The paper based materials may be embedded into a chip and an electronic reader may be included. The paper based materials with the reactions may not be reusable.

III. Operation

Figure 4:
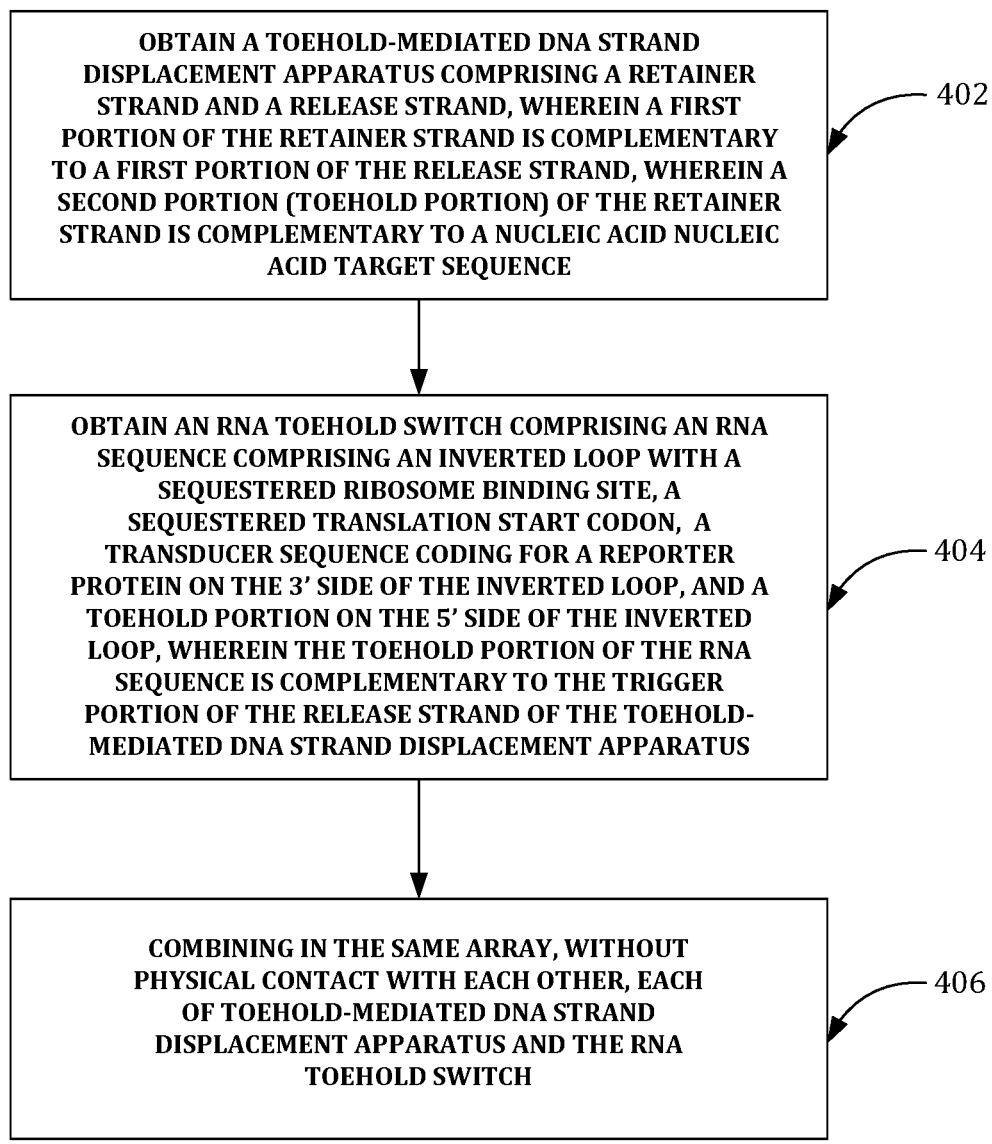
FIG. 4 illustrates a flow chart of a method of facilitating detection of a nucleic acid target sequence in accordance with some embodiments.

FIG. 4 is a flow chart setting forth the general stages involved in a method 400 consistent with an embodiment of the disclosure for facilitating detection of a nucleic acid target sequence. Method 200 may be implemented using a computing device 700 as described in more detail below with respect to FIG. 7.

Although method 400 has been described to be performed by apparatus 100, it should be understood that computing device 700 may be used to perform the various stages of method 400. Furthermore, in some embodiments, different operations may be performed by different networked elements in operative communication with computing device 700. For example, server 110 may be employed in the performance of some or all of the stages in method 400. Moreover, server 110 may be configured much like computing device 700. The server may be a part of, for example, comprise cloud computing platform.

Although the stages illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart may be, in various embodiments, performed in arrangements that differ from the ones illustrated. Moreover, various stages may be added or removed from the flow charts without altering or deterring from the fundamental scope of the depicted methods and systems disclosed herein. Ways to implement the stages of method 400 will be described in greater detail below.

The method 400 may facilitate detection of the nucleic acid target sequence. For instance, the nucleic acid target sequence may correspond to a RNA and/or a single stranded DNA. Further, the nucleic acid target sequence may include a SNP genotype.

The method 400 may include a step 402 of obtaining a toehold-mediated DNA strand displacement apparatus, as exemplarily illustrated in FIG. 3A, including a retainer strand 302 and a release strand 304. A first portion 302a of the retainer strand 302 may be complementary to a first portion 304a of the release strand 304. Accordingly, the retainer strand 302 and the release strand 304 may be bound together at the first portions 302a and 304a. Further, a second portion (toehold portion) 302b of the retainer strand 302 may be complementary to the nucleic acid target sequence (not shown in figure). Further, the second portion (toehold portion) 302b of the retainer strand 302 may be distinct from the first portion 302a of the retainer strand 302. Likewise, the second portion (trigger portion) 304b of the release strand 304 may be distinct from the first portion 304a of the release strand 304. Accordingly, subsequent to binding of the retainer strand 302 and the release strand 304, the second portions 302b and 304b may be overhanging as illustrated. The retainer strand may also have a Poly A sequence attached to it on the overhanging side, beyond the toehold region. If a bead or some other anchor is used that has a Poly T sequence, it can bind to the Poly A sequence and hold the retainer strand in place.

The method 400 may further include a step 406 of obtaining a RNA toehold switch, as illustrated in FIG. 3B, including an RNA sequence. It is to be understood from the present disclosure that such reference to FIG. 3B is a reference to one possible embodiment, and that sequestration is not required to be through inner loops of the inverted loop, but can also be enabled via, for example, hybridization. Further, the RNA sequence may include an inverted loop with a sequestered ribosome binding site 306 and a sequestered translation start codon 308, a transducer sequence 310 coding for a reporter protein, located on the 3' side of the inverted loop, and a toehold portion 312 that is complementary to the trigger portion of the release strand of the toehold-mediated DNA strand displacement apparatus. In some embodiments, the reporter protein may include, but is not limited to, one or more of beta-galactosidase and Green Fluorescent Protein (GFP). Further, if beta-galactosidase is used for a colorimetric assay, one or more chemicals may be added to the substrate so that beta-galactosidase can react with the one or more chemicals to produce a color change. Further, the toehold portion 312 of the RNA sequence is complementary to the second portion 304b of the release strand 304 of the toehold-mediated DNA strand displacement apparatus. Accordingly, the release strand 304 may be configured to bind with the RNA toehold switch at the toehold portion 312.

Additionally, the method 400 may include a step 406 of combining each of toehold-mediated DNA strand displacement apparatus and the RNA toehold switch in an assay such that they are never in direct contact with each other but such that when a nucleic acid target sequence complementary to both the first portion and the toehold portion of the retainer strand is present, the release strand is displaced and may travel to the RNA toehold switch, after which the trigger portion of the release strand binds to the toehold portion of the RNA toehold switch, which leads to the collapse of the RNA toehold switch, allowing for the expression of a reporter protein.

Figure 1B:
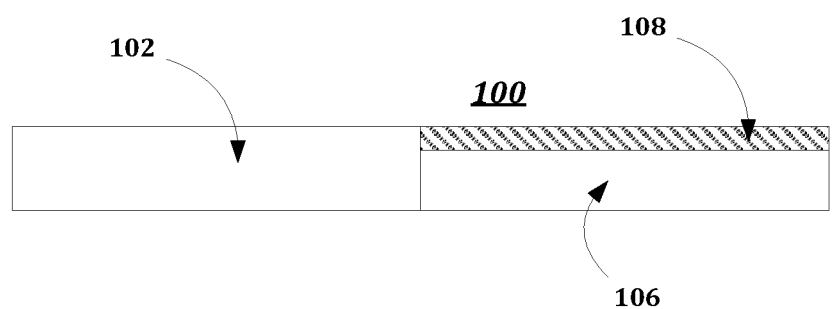
FIG. 1B illustrates a side view of an array for facilitating detection of a nucleic acid target sequence in accordance with some embodiments.

For instance, in some embodiments, the combining may include embedding each of the toehold-mediated DNA strand displacement apparatus and the RNA toehold switch on a substrate 104, as exemplarily illustrated in FIG. 1A-1B. For instance, the substrate 104 may include a paper based material that may be freeze dried. Further, the substrate 104 may include a cell extract configured to facilitate expression of the reporter protein. For example, the cell extract may include S30 cell extract.

In another instance, the combining may include allowing fluid to flow between the toehold mediated DNA strand displacement apparatus and the RNA toehold switch. For example, such a phenomenon may be allowed to take place in a microfluidic device. Accordingly, the toehold-mediated DNA strand displacement apparatus may be contained in a first chamber of the microfluidic device. Further, the RNA toehold switch may be contained in a second chamber of the microfluidic device. Moreover, the first chamber may be spatially separated from the second chamber. Furthermore, a flow of contents from the first chamber to the second chamber may be unidirectional. Accordingly, diffusion of the contents of the fluid from the second chamber back into the first chamber may be eliminated and/or minimized.

Further, in some embodiments, the method 400 may further include a step of assembling a plurality of substrates 104 in an array 106 as exemplarily illustrated in FIG. 1A-1B. The plurality of substrates 104 may be partitioned using a demarcation material, such as for example, but not limited to, a wax based ink. Additionally, a first substrate 104a of the plurality of substrates 104 may be configured to detect a first nucleic acid target sequence. Further, a second substrate 104b of the plurality of substrates 104 may be configured to detect a second nucleic acid target sequence. Accordingly, in some instances, the array 106 may be capable of simultaneously detecting multiple distinct nucleic acid target sequences.

Further, in some embodiments, the method 400 may additionally include a step of obtaining a specimen comprising the sample. Furthermore, the method 400 may include a step of subjecting the specimen to each of DNA extraction, DNA denaturation, and DNA fragmentation. Accordingly, single nucleic acid strands containing the nucleic acid target sequence may be generated. Alternatively, in case the specimen includes RNA, the specimen may be subjected to RNA extraction and RNA strand separation.

Additionally, the method 400 may further include introducing a sample comprising the nucleic acid target sequence onto the substrate 104. Accordingly, binding of the nucleic acid target sequence to second portion 302b of the retainer strand 302 may displace the release strand 304. Further, the second nucleic strand 304 may bind to the RNA toehold switch resulting in unwinding of the inverted loop, exposure of the sequestered ribosome binding site 306 and translation of the reporter protein.

Accordingly, in some embodiments, the method 400 may further include a step of detecting presence of the reporter protein using an electronic reader 108, as exemplarily illustrated in FIG. 1B. The presence of the reporter protein may be indicative of detection of the nucleic acid target sequence. Furthermore, the method 400 may include a step of communicating detection of the reporter protein to a computing device, such as for example a smartphone and/or a desktop computer. Accordingly, further analysis of detection of the nucleic acid target sequence may be performed. Alternatively, presence of the reporter protein may also be detected based on visual inspection by eye. For instance, the reporter protein may react with one or more chemicals present in the substrate leading to a colorimetric change in the substrate which may be visible in plain sight.

Figure 5:
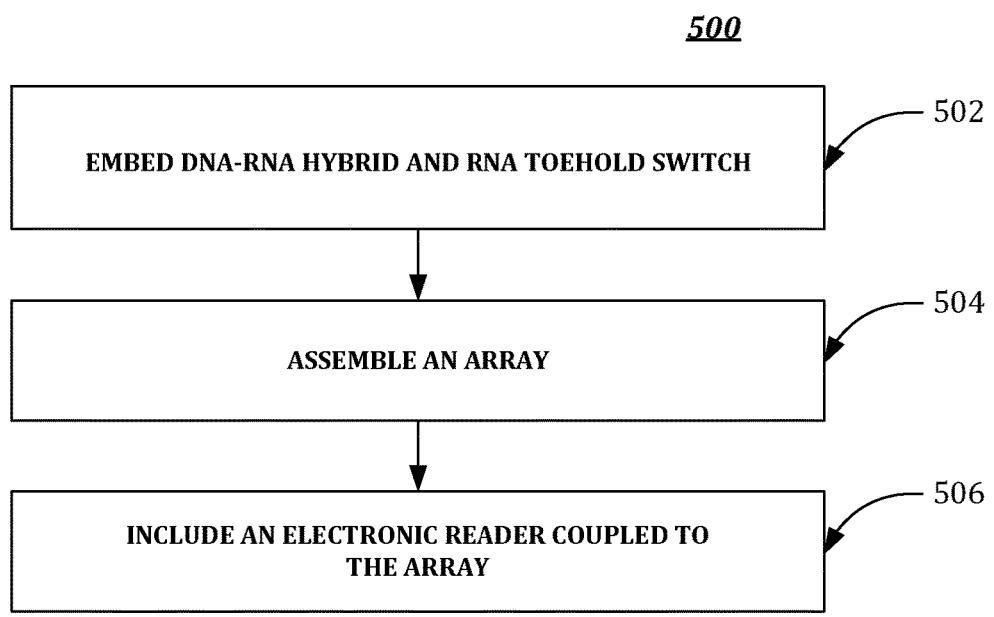
FIG. 5 illustrates a flow chart of a method of manufacturing an array configured to facilitate detection of a nucleic acid target sequence in accordance with some embodiments.

Referring to FIG. 5, a flow chart of a method 500 of manufacturing an array 106 configured to facilitate detection of a nucleic acid target sequence, in accordance with some embodiments is illustrated. The method 500 may include a step of embedding toehold-mediated DNA strand displacement apparatus and RNA toehold switch onto a paper based material containing a cell extract for translation. Further, the method 500 may include a step of assembling paper based materials into the array 106 with individual paper based materials separated by a demarcation material, such as for example, but not limited to, a wax based ink. Furthermore, the method 500 may comprise a step of including the electronic reader 108 coupled to the array 106.

Figure 6:
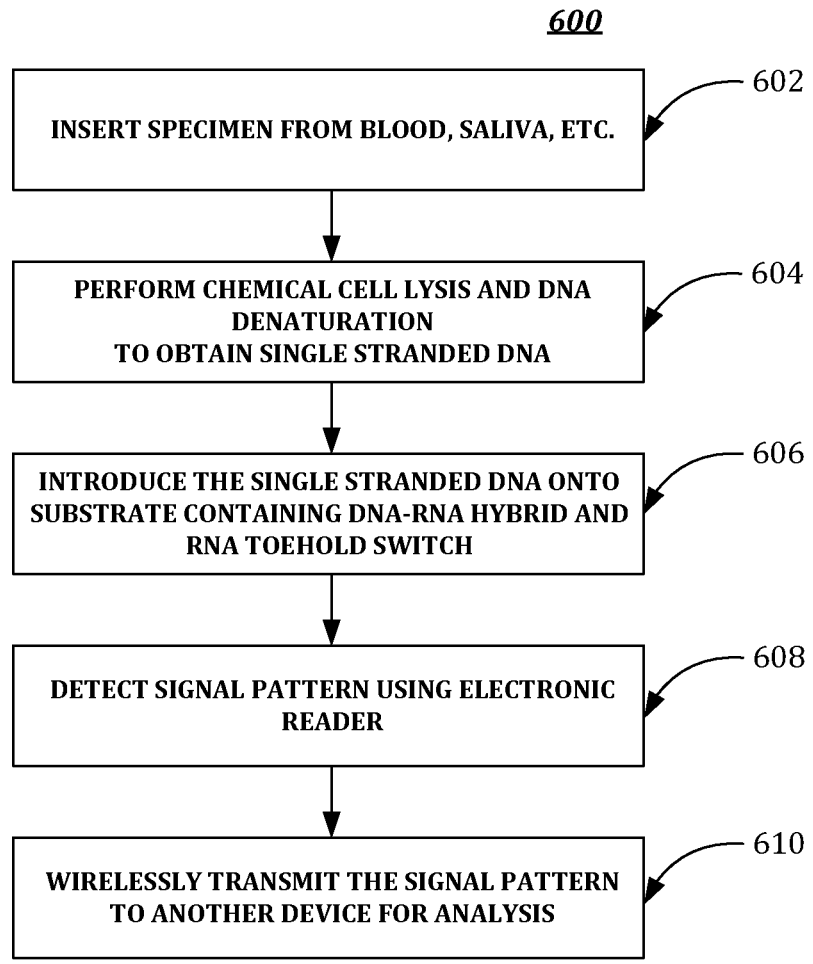
FIG. 6 illustrates a flow chart of a method of performing genotyping of a specimen in accordance with some embodiments.

Turning now to FIG. 6, a flow chart of a method 600 of performing genotyping of a specimen in accordance with some embodiments is illustrated. The method 600 may include a step 602 of inserting a specimen from blood, saliva, bodily tissues, bone marrow, etc. into the apparatus 100. Further, the method 600 may include a step 604 of performing chemical cell lysis and DNA denaturation to obtain single stranded DNA. Additionally, the method 600 may include a step 606 of introducing the single stranded DNA onto substrate 104 containing toehold-mediated DNA strand displacement apparatus and RNA toehold switch. Further, the method 600 may include a step 608 of detecting a signal pattern using electronic reader 108. Furthermore, the method 600 may include a step 610 of wirelessly transmitting the signal pattern to another device, such as a smartphone and/or a computer for further analysis.

IV. Application

Potential applications of the embodiment's disclosure herein include genotyping for SNPs linked to disease risk inheritance, to drug effectiveness or adverse reactions, or to the presence of certain pathogens; or for paternity/immigration testing. One benefit may be the relatively low cost of manufacturing and the potential of it being used in a portable point-of-care device available to consumers or in medical or legal settings.

An example of using it for genetic testing could be selling relatively cheap paper arrays with that test for specific diseases, and a separate DNA extraction device into which the paper arrays are placed. The customer extracts saliva and places it in the abovementioned apparatus using a swab. The paper array can be ejected from the apparatus once the reactions are completed (similar idea to printing a Polaroid photo), and the customer can study the visual pattern in the array to obtain the results.

Embodiments may require manufacturing multiple paper arrays each testing for a few loci, so that each array is more easily interpreted by the customer. For example, there could be a paper array testing specifically for genes linked to Parkinson's disease and separate arrays testing for genes related to Alzheimer's disease, cancers, etc. Embodiments may also require making the reporter protein one that can be visualized without an electronic reader. Overall, embodiments may enable a user to take genetic testing to the do-it-yourself level. Appropriate safety measures would have to be in place.

Another potential application of the embodiments disclosed herein may pertain to genetic testing could be selling a coupled DNA extraction/electronic reader device (e.g., the aforementioned apparatus) with the genotyping array embedded in it. Customers may insert their saliva into the device using a swab and a few hours later obtain the results on their account online. The benefit from existing genotyping tests such as 23Andme™ is that the process does not involve mailing the saliva or waiting long for the results. This kind of device could be bought online or from a pharmacy. In other embodiments, the test could be done at a pharmacy, such as at the Minute Clinic™ at CVS™. Additionally, there may be the potential that embodiments could be done at a medical setting as part of routine testing if requested, such as for testing of SNP's related to drug response, or for testing of SNP's associated with certain infectious diseases.

The invention may be used for paternity testing as well. This would require choosing SNPs that can accurately distinguish between individuals in a given population. The device with the electronic reader, DNA extraction functionality, and SNP genotyping array could be used in the same way as for disease risk testing, but instead the paternity results get uploaded to the customer's account. A test like this may be bought at a pharmacy as a product, done at a the pharmacy as a service, used at laboratories as a cheaper device, or used in legal settings for immigration testing and other forensics applications.

IV. Device Architecture

Embodiments of the present disclosure may comprise an apparatus having a processing unit and memory storage embedded therein. The processing unit coupled to the memory storage, wherein the processing unit, in conjunction with other sensing components, may be configured to provide the functionality disclosed above.

Figure 7:
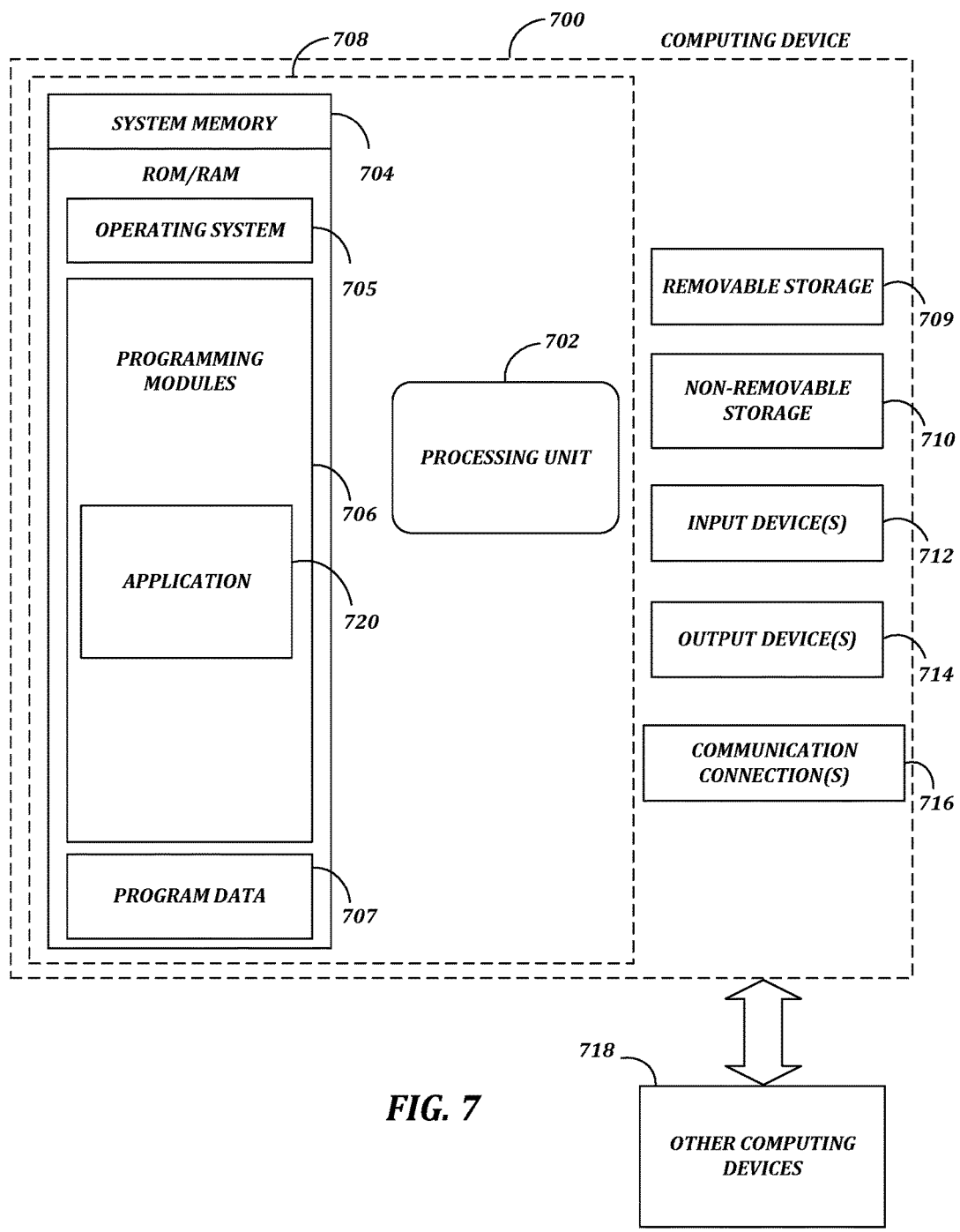
FIG. 7 is a block diagram of a system including a computing device for performing one or more of methods of FIG. 4 to FIG. 6.

FIG. 7 is a block diagram of a system including computing device 700. The computing device may be, for example, the electronic reader 108 as illustrated in FIG. 1B. In other instances, the computing device 700 may be, for example, the smartphone and/or the desktop computer communicatively coupled to the apparatus 100 as described in FIG. 2. Consistent with an embodiment of the disclosure, the aforementioned memory storage and processing unit may be implemented in a computing device, such as computing device 700 of FIG. 7. Any suitable combination of hardware, software, or firmware may be used to implement the memory storage and processing unit. For example, the memory storage and processing unit may be implemented with computing device 700 or any of other computing devices 718, in combination with computing device 700. The aforementioned system, device, and processors are examples and other systems, devices, and processors may comprise the aforementioned memory storage and processing unit, consistent with embodiments of the disclosure.

With reference to FIG. 7, a system consistent with an embodiment of the disclosure may include a computing device, such as computing device 700. In a basic configuration, computing device 700 may include at least one processing unit 702 and a system memory 704. Depending on the configuration and type of computing device, system memory 704 may comprise, but is not limited to, volatile (e.g. random access memory (RAM)), nonvolatile (e.g. read-only memory (ROM)), flash memory, or any combination. System memory 704 may include operating system 705, one or more programming modules 706, and may include a program data 707. Operating system 705, for example, may be suitable for controlling computing device 700's operation. In one embodiment, programming modules 706 may include application 720. Furthermore, embodiments of the disclosure may be practiced in conjunction with a graphics library, other operating systems, or any other application program and is not limited to any particular application or system. This basic configuration is illustrated in FIG. 7 by those components within a dashed line 708.

Computing device 700 may have additional features or functionality. For example, computing device 700 may also include additional data storage devices (removable and/or non-removable) such as, for example, magnetic disks, optical disks, or tape. Such additional storage is illustrated in FIG. 7 by a removable storage 709 and a non-removable storage 710. Computer storage media may include volatile and nonvolatile, removable and non-removable media implemented in any method or technology for storage of information, such as computer readable instructions, data structures, program modules, or other data. System memory 704, removable storage 709, and non-removable storage 710 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 700. Any such computer storage media may be part of device 700. Computing device 700 may also have input device(s) 712 such as a keyboard, a mouse, a pen, a sound input device, a touch input device, etc. Output device(s) 714 such as a display, speakers, a printer, etc. may also be included. The aforementioned devices are examples and others may be used.

Computing device 700 may also contain a communication connection 716 that may allow device 700 to communicate with other computing devices 718, such as over a network in a distributed computing environment, for example, an intranet or the Internet. Communication connection 716 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 704, including operating system 705. While executing on processing unit 702, programming modules 706 (e.g., application 720) may perform processes including, for example, one or more of the stages as described above. The aforementioned process is an example, and processing unit 702 may perform other processes. Other programming modules that may be used in accordance with embodiments of the present disclosure may include electronic mail and contacts applications, word processing applications, spreadsheet applications, database applications, slide presentation applications, drawing or computer-aided application programs, etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, multiprocessor systems, microprocessor-based or programmable consumer electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random access memory (RAM), a read-only memory (ROM), an erasable programmable read-only memory (EPROM or Flash memory), and an optical fiber. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), a carrier wave from the Internet, or other forms of RAM or ROM. Further, the disclosed methods' stages may be modified in any manner, including by reordering stages and/or inserting or deleting stages, without departing from the disclosure.

V. Claims

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as example for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A method of facilitating detection of a nucleic acid target sequence, the method comprising:
    utilizing a toehold-mediated DNA strand displacement apparatus comprising a retainer strand and a release strand, wherein a first portion of the retainer strand is complementary to a first portion of the release strand, wherein a second portion (toehold portion) of the retainer strand is complementary to the nucleic acid target sequence, wherein the second portion (trigger portion) of the release strand is overhanging;
    utilizing a RNA toehold switch comprising a RNA sequence comprising an inverted loop with a sequestered ribosome binding site, a sequestered translation start codon, a transducer sequence coding for a reporter protein on the 3' side of the inverted loop, and a toehold portion on the 5' side of the inverted loop, wherein the toehold portion of the RNA sequence is complementary to the trigger portion of the release strand of the toehold-mediated DNA strand displacement apparatus;
    wherein utilizing the toehold-mediated DNA strand displacement apparatus and the RNA toehold switch comprises combining each of the toehold-mediated DNA strand displacement apparatus and the RNA toehold switch in an assay such that they are never in direct contact with each other but such that when the nucleic acid target sequence complementary to both the first portion and the toehold portion of the retainer strand is present, the release strand is displaced and may travel to the RNA toehold switch, after which the trigger portion of the release strand binds to the toehold portion of the RNA toehold switch, which leads to the collapse of the RNA toehold switch, allowing for the expression of a reporter protein; and
    detecting presence of the reporter protein using at least one from the group of the following: plain sight visibility and an electronic reader;
    wherein presence of the reporter protein is indicative of detection of the nucleic acid target sequence.

2. The method of claim 1, wherein the toehold-mediated DNA strand displacement is anchored to a substrate, such that it is never in direct contact with the RNA toehold switch; wherein the anchor attaches the retainer strand, but not the release strand, to the substrate.

3. The method of claim 2, wherein the substrate is paper, silica, glass, or polydimethylsiloxane (PDMS).

4. The method of claim 2, wherein the anchor is a bead.

5. The method of claim 4, wherein the bead is a polystyrene bead.

6. The method of claim 1, wherein the retainer strand of the toehold-mediated DNA strand displacement apparatus contains a poly A sequence.

7. The method of claim 6, wherein the Poly A sequence binds to a poly T sequence attached to an anchor.

8. The method of claim 1, wherein the RNA toehold switch is combined with a cell free extract configured to facilitate expression of the reporter protein.

9. The method of claim 8, wherein the RNA toehold switch and the cell free extract are dried and stored within a substrate.

10. The method of claim 9, wherein the fibrous substrate is a paper-based material.

11. The method of claim 10, wherein the paper-based material is chromatography paper or cellulose filter paper.

12. The method of claim 8, wherein the RNA toehold switch and the cell free extract are combined in a solution in vitro.

13. The method of claim 8, wherein the cell extract comprises S30 cell extract.

14. The method of claim 1, wherein the toehold-mediated DNA strand displacement apparatus is contained in a first chamber of a microfluidic device, wherein the RNA toehold switch is contained in a second chamber of the microfluidic device, wherein the first chamber is spatially separated from the second chamber, wherein a flow of contents from the first chamber and the second chamber is unidirectional.

15. The method of claim 1, wherein the nucleic acid target sequence corresponds to at least one of a RNA and a single stranded DNA.

16. The method of claim 1, wherein the reporter protein comprises at least one of beta-galactosidase and Green Fluorescent Protein (GFP).

17. The method of claim 16, wherein the reporter protein comprises beta-galactosidase, wherein the RNA toehold switch is combined with both the cell free extract and a chemical that changes color upon reaction with beta-galactosidase.

18. The method of claim 1 further comprising assembling a plurality of substrates in an array, wherein the plurality of substrates are partitioned using a demarcation material, wherein a first substrate is configured to detect a first nucleic acid target sequence, wherein a second substrate is configured to detect a second nucleic acid target sequence.

19. The method of claim 1 further comprising:
obtaining a specimen comprising the sample; and
subjecting the specimen to each of DNA extraction, DNA denaturation, and DNA fragmentation.

* * * * *